(12) United States Patent
Huang

(10) Patent No.: US 7,796,732 B2
(45) Date of Patent: Sep. 14, 2010

(54) X-RAY IMAGING SYSTEM AND X-RAY IMAGING METHOD

(75) Inventor: Yannan Huang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 174 days.

(21) Appl. No.: 12/118,228

(22) Filed: May 9, 2008

(65) Prior Publication Data

US 2008/0279331 A1 Nov. 13, 2008

(51) Int. Cl.
*G21K 5/10* (2006.01)
(52) U.S. Cl. .......................................... 378/68
(58) Field of Classification Search ............. 378/20, 378/62–65, 68, 195, 208
See application file for complete search history.

(56) References Cited

U.S. PATENT DOCUMENTS

| | | | |
|---|---|---|---|
| 3,891,856 A | 6/1975 | Amor, Jr. et al. | |
| 4,097,746 A | 6/1978 | Ingham et al. | |
| 4,334,155 A | 6/1982 | Gieschen et al. | |
| 4,356,400 A | 10/1982 | Polizzi et al. | |
| 4,435,830 A | 3/1984 | Suzuki et al. | |
| 4,501,011 A | 2/1985 | Hauck et al. | |
| 4,894,855 A | 1/1990 | Kresse | |
| 5,023,899 A | 6/1991 | Ohlson | |
| 5,048,070 A | 9/1991 | Machama et al. | |
| 6,027,247 A | 2/2000 | Tachi et al. | |
| 6,056,437 A | 5/2000 | Toth | |
| 6,155,713 A | 12/2000 | Watanabe | |
| 6,634,790 B1 | 10/2003 | Salter, Jr. | |
| 6,856,826 B2 * | 2/2005 | Seeley et al. | 600/426 |
| 7,182,511 B2 | 2/2007 | Boomgaarden et al. | |
| 7,263,172 B2 | 8/2007 | Grunau | |
| 2007/0238957 A1 * | 10/2007 | Yared | 600/407 |

FOREIGN PATENT DOCUMENTS

JP 11236150 8/1999

* cited by examiner

*Primary Examiner*—Irakli Kiknadze
(74) *Attorney, Agent, or Firm*—Armstrong Teasdale LLP

(57) ABSTRACT

An X-ray imaging system is disclosed which can effect positioning of an X-ray irradiator and an X-ray receiver in an adaptive manner. The X-ray imaging system uses an X-ray irradiator and an X-ray receiver opposed to each other through a space to radiograph a subject positioned between the two and comprises radiographing device having the X-ray irradiator and the X-ray receiver, optical radiographing device for picking up an optical image of the subject, specifying device for analyzing the optical image and specifying physical characteristics of the subject, and positioning device for positioning the X-ray irradiator and the X-ray receiver of the radiographing device on the basis of the specified physical characteristics and a portion to be radiographed of the subject.

20 Claims, 7 Drawing Sheets

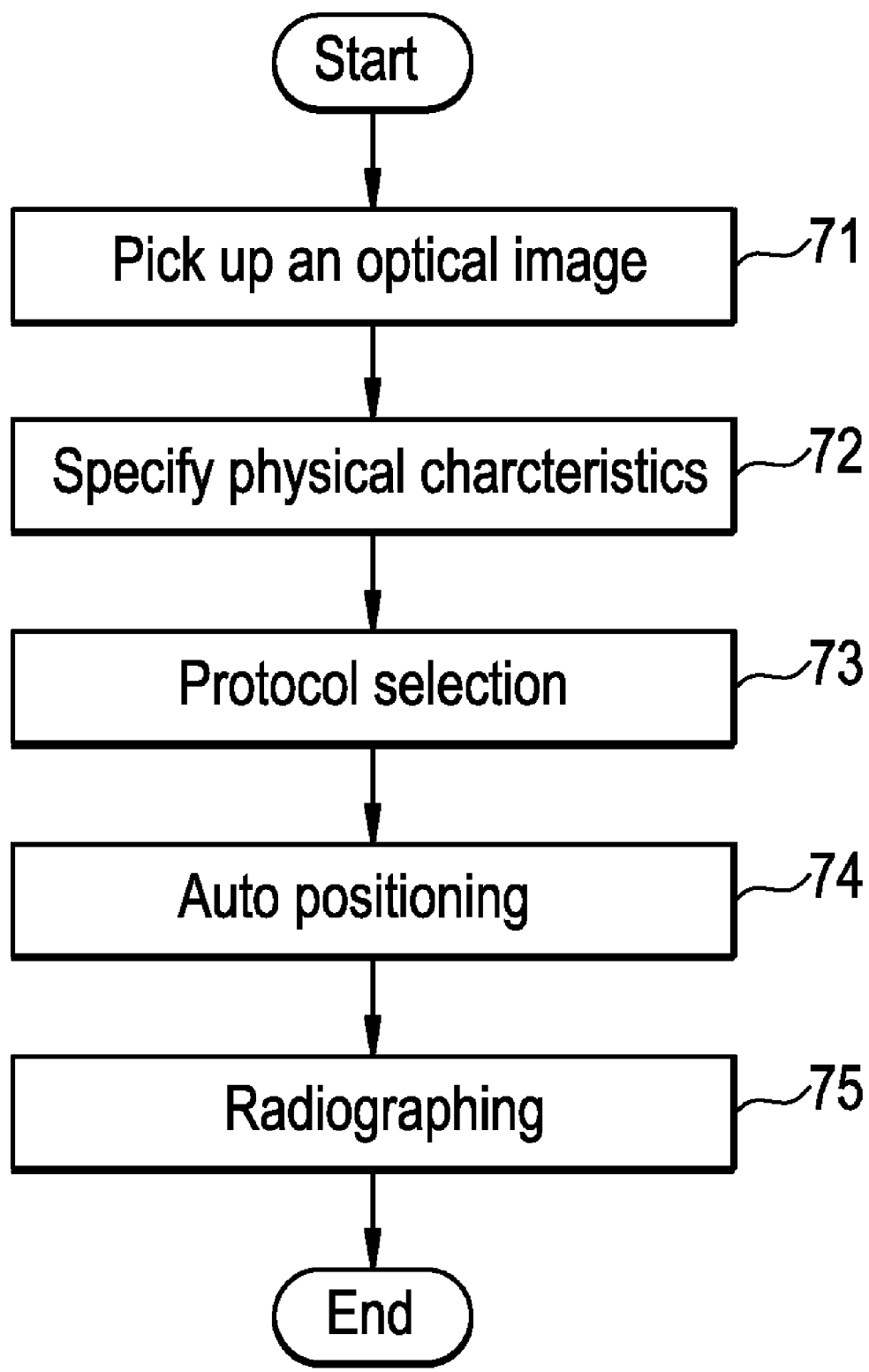

X-RAY IMAGING SYSTEM AND X-RAY IMAGING METHOD

CROSS REFERENCE TO RELATED APPLICATIONS

This application claims the benefit of Chinese Patent Application No. 200710102911.5 filed May 11, 2007, and incorporated herein in its entirety.

BACKGROUND OF THE INVENTION

The subject matter disclosed herein relates to an X-ray imaging system and more particularly to an X-ray imaging system using an X-ray irradiator and an X-ray receiver opposed to each other through a space to radiograph a subject positioned between the two.

In an X-ray imaging system there are used an X-ray irradiator and an X-ray receiver opposed to each other through a space to radiograph a subject positioned between them. Positioning of the X-ray irradiator and the X-ray receiver is performed in the X-ray imaging system. The positioning is effected by adjusting the position and attitude of each of the X-ray irradiator and the X-ray receiver to match the constitution of the subject and a portion to be radiographed of the subject (see, for example, Japanese Unexamined Patent Publication No. Hei 10 (1998)-057360).

Among X-ray imaging systems there is one wherein positioning of an X-ray irradiator and that of an X-ray receiver is performed automatically. However, since this positioning is an automatic positioning to a preset default state, it is impossible to cope with an individual difference between subjects.

Accordingly, it is an object of the present invention to provide an X-ray imaging system which carries out positioning of an X-ray irradiator and that of an X-ray receiver in an adaptive manner.

SUMMARY OF THE INVENTION

According to the present invention for solving the above-mentioned problem there is provided an X-ray imaging system using an X-ray irradiator and an X-ray receiver opposed to each other through a space to radiograph a subject positioned between the two, the X-ray imaging system comprising radiographing device having the X-ray irradiator and the X-ray receiver, optical radiographing device for picking up an optical image of the subject, specifying device for analyzing the optical image and specifying physical characteristics of the subject, and positioning device for positioning the X-ray irradiator and the X-ray receiver of the radiographing device on the basis of the specified physical characteristics and a portion to be radiographed of the subject.

It is preferable in point of effective positioning that the radiographing device comprise: first support device for supporting the X-ray irradiator movably in two horizontal directions orthogonal to each other and also in the vertical direction and rotatably about two axes orthogonal to each other; and second support device for supporting the X-ray receiver vertically movably and in such a manner as the direction of a light receiving surface being changeable.

It is preferable in point of effective positioning that the radiographing device comprise: first support device for supporting the X-ray irradiator movably in two horizontal directions orthogonal to each other and also in the vertical direction and rotatably about two axes orthogonal to each other; and a table for supporting a top board as a subject carrier vertically movably and supporting the X-ray receiver under the top board horizontally movably.

It is preferable in point of effective positioning that the radiographing device comprise first support device for supporting the X-ray irradiator movably in two horizontal directions orthogonal to each other and also in the vertical direction and rotatably about two axes orthogonal to each other, second support device for supporting the first X-ray receiver vertically movably and in such a manner as the direction of a light receiving surface being changeable, and a table for supporting a top board as a subject carrier vertically movably and supporting the second X-ray receiver under the top board horizontally movably.

It is preferable in point of effectively positioning the X-ray irradiator that the first support device be an overhead tube suspension.

it is preferable in point of effectively positioning the X-ray detector that the second support device be a wall stand.

The X-ray imaging system according to the present invention uses an X-ray irradiator and an X-ray receiver opposed to each other through a space to radiograph a subject positioned between the two and comprises radiographing device having the X-ray irradiator and the X-ray receiver, optical radiographing device for picking up an optical image of the subject, specifying device for analyzing the optical image and specifying physical characteristics of the subject, and positioning device for positioning the X-ray irradiator and the X-ray receiver of the radiographing device on the basis of the specified physical characteristics and a portion to be radiographed of the subject. Therefore, the X-ray imaging system can effect positioning of the X-ray irradiator and that of the X-ray receiver in an adaptive manner.

BRIEF DESCRIPTION OF THE DRAWINGS

FIG. 7 is a flow chart showing operations of the X-ray imaging system as an example of the best mode for carrying out the present invention.

DETAILED DESCRIPTION OF THE INVENTION

Figure 1:
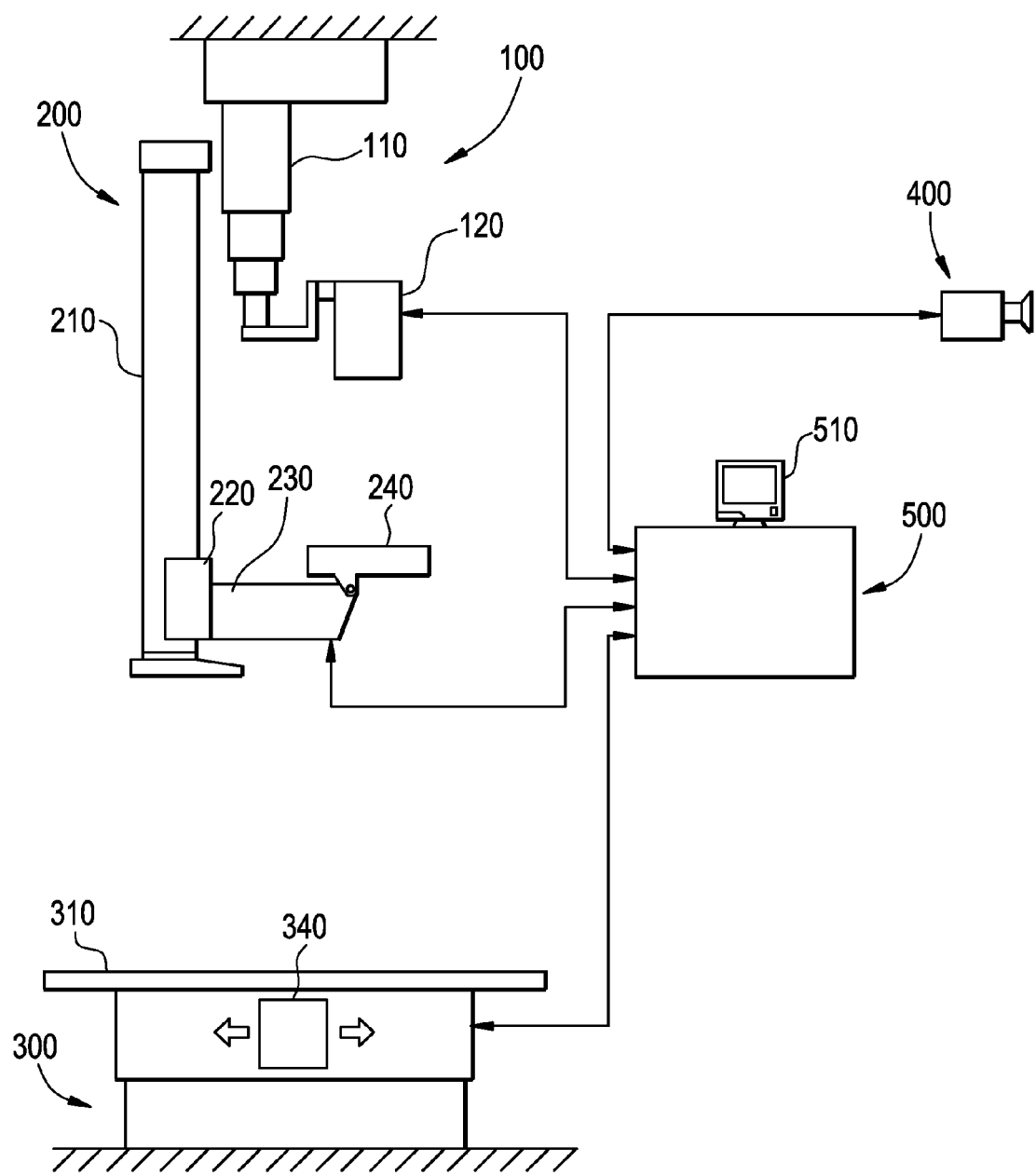
FIG. 1 is a diagram showing the configuration of an X-ray imaging system according to an example of the best mode for carrying out the present invention.

The best mode for carrying out the invention will be described in detail hereinunder with reference to the drawings. The present invention is not limited to the best mode for carrying out the invention. FIG. 1 shows a schematic configuration of an X-ray imaging system. This system is an example of the best mode for carrying out the invention. With the configuration of this system there is shown an example of the best mode for carrying out the invention in connection with the X-ray imaging system.

As shown in FIG. 1, this system has an X-ray irradiating unit 100, an X-ray receiving unit 200, a radiographing table 300, a camera 400 and an operator console 500. The section comprising the X-ray irradiating unit 100, X-ray receiving unit 200 and radiographing table 300 is an example of the radiographing device in the present invention. The camera 400 is an example of the optical photographing device in the present invention.

The X-ray irradiating unit 100 is configured to support an X-ray irradiator 120 at a lower end of a column 110 hanging from a ceiling. Such a support mechanism is also called an overhead tube suspension. The overhead tube suspension is an example of the first support device in the present invention. The X-ray irradiator 120 is an example of the X-ray irradiator in the present invention.

Figure 2:
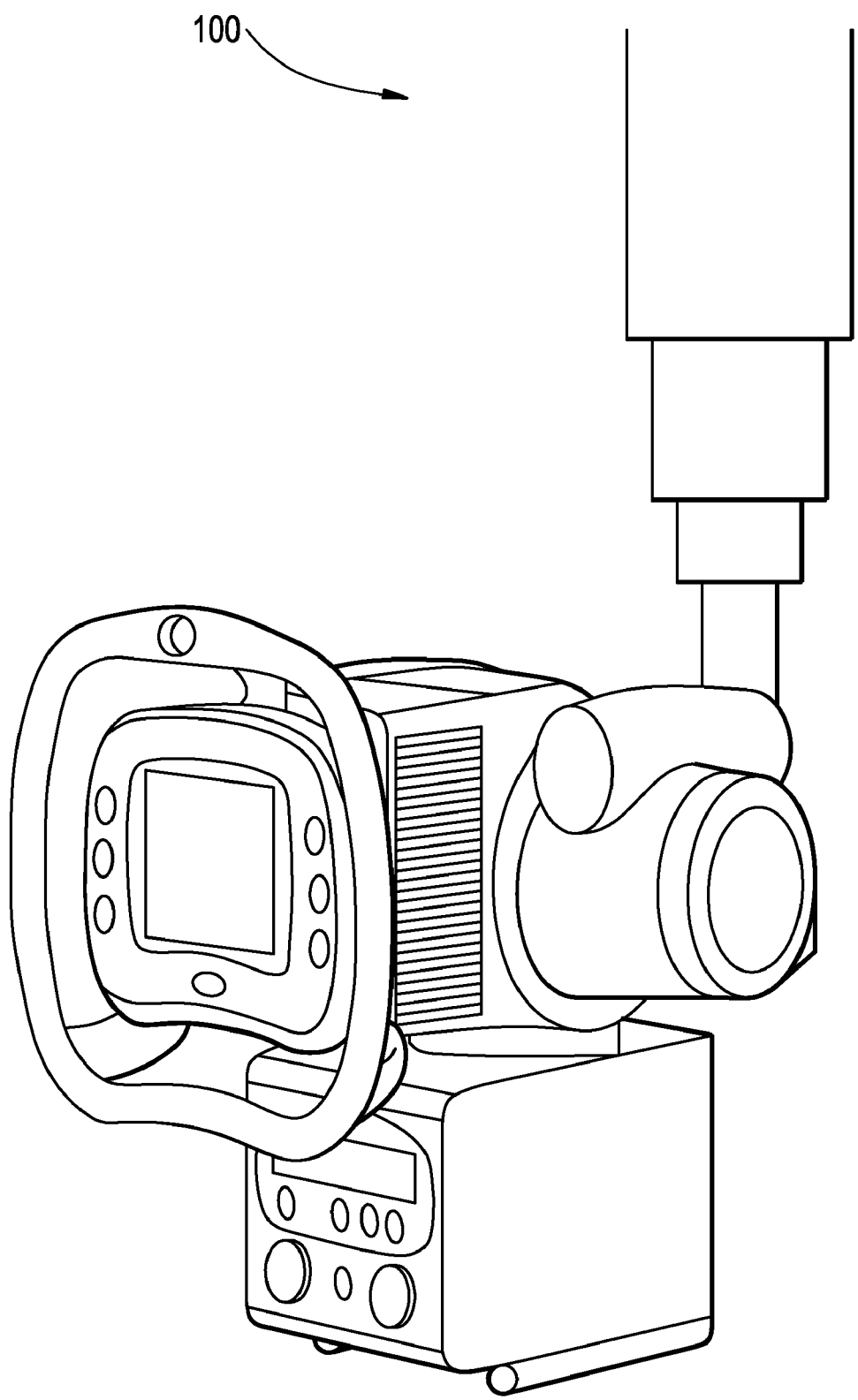
FIG. 2 is a diagram showing an example of the appearance of an X-ray irradiating unit.

The column 110 can extend and contract in the vertical direction and is movable horizontally along the ceiling. The direction of horizontal moving is two directions orthogonal to each other. At the lower end of the column 110 the X-ray irradiator 120 is rotatable about two axes orthogonal to each other. The extension and contraction, as well as the horizontal movement in two directions, of the column 110 and the biaxial rotation of the X-ray irradiator 120 are each performed by utilizing power of a motor for example. FIG. 2 shows the appearance of an example of the X-ray irradiating unit 100.

The X-ray receiving unit 200 is configured in such a manner that a carriage 220 is supported vertically movably by a column 210 perpendicular to a floor, an arm 230 is supported horizontally by the carriage 220, and a first X-ray receiver 240 is supported by a front end of the arm 230. Such a support mechanism is also called a wall stand. The wall stand is an example of the second support device in the present invention. The X-ray receiver 240 is an example of the X-ray receiver in the present invention.

Figure 3:
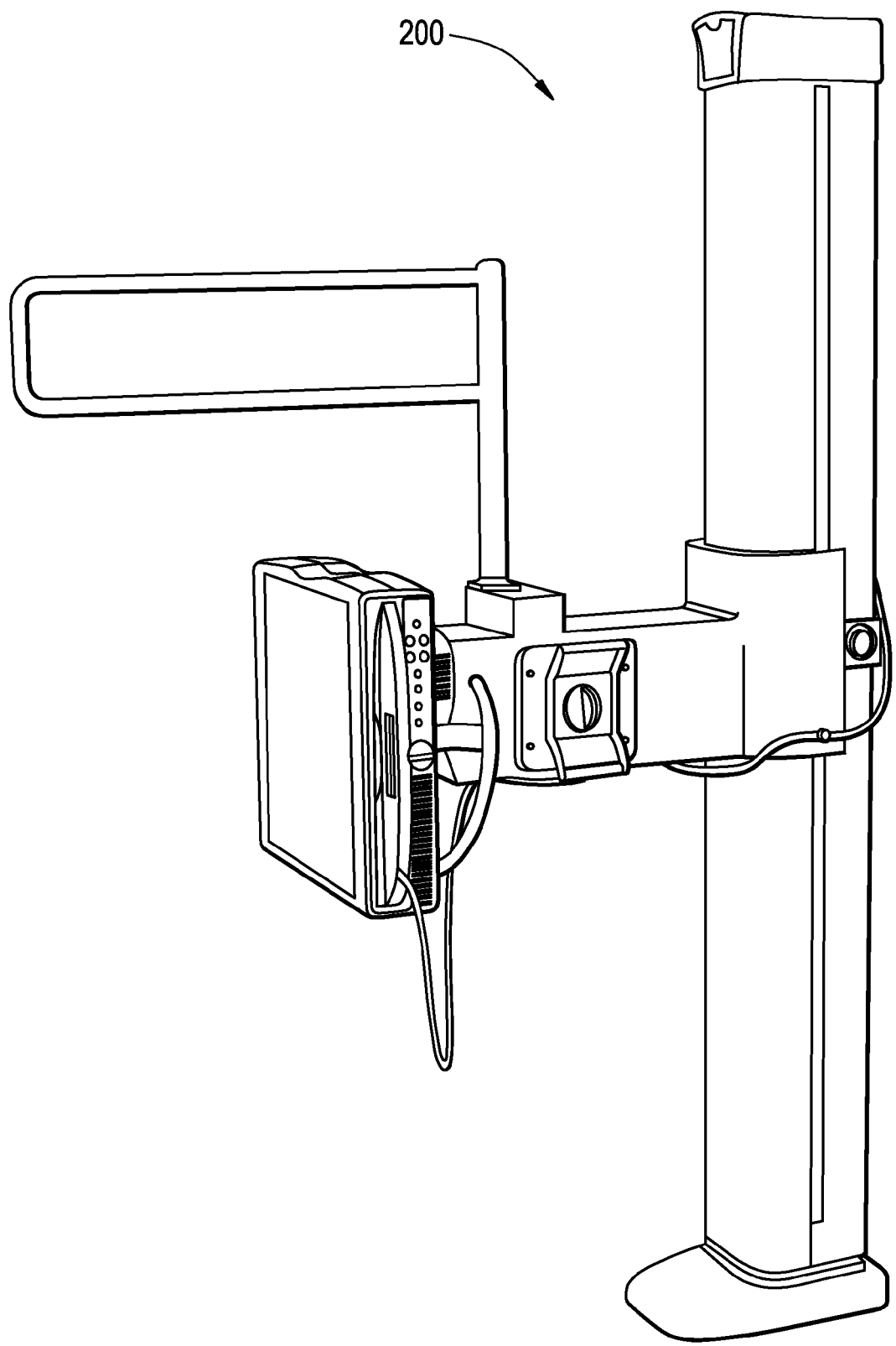
FIG. 3 is a diagram showing an example of the appearance of an X-ray receiving unit.

The X-ray receiver 240 is a flat plate-like structure and the direction of a light receiving surface thereof can be changed to match an incidence direction of X-ray. The direction of the light receiving surface is typically horizontal or vertical, but this constitutes no limitation and there may be adopted any other direction. The vertical movement of the carriage 220 and changing the direction of the light receiving surface of the first X-ray receiver 240 are each performed by utilizing power of a motor for example. FIG. 3 shows the appearance of an example of the X-ray receiving unit 200.

Figure 4:
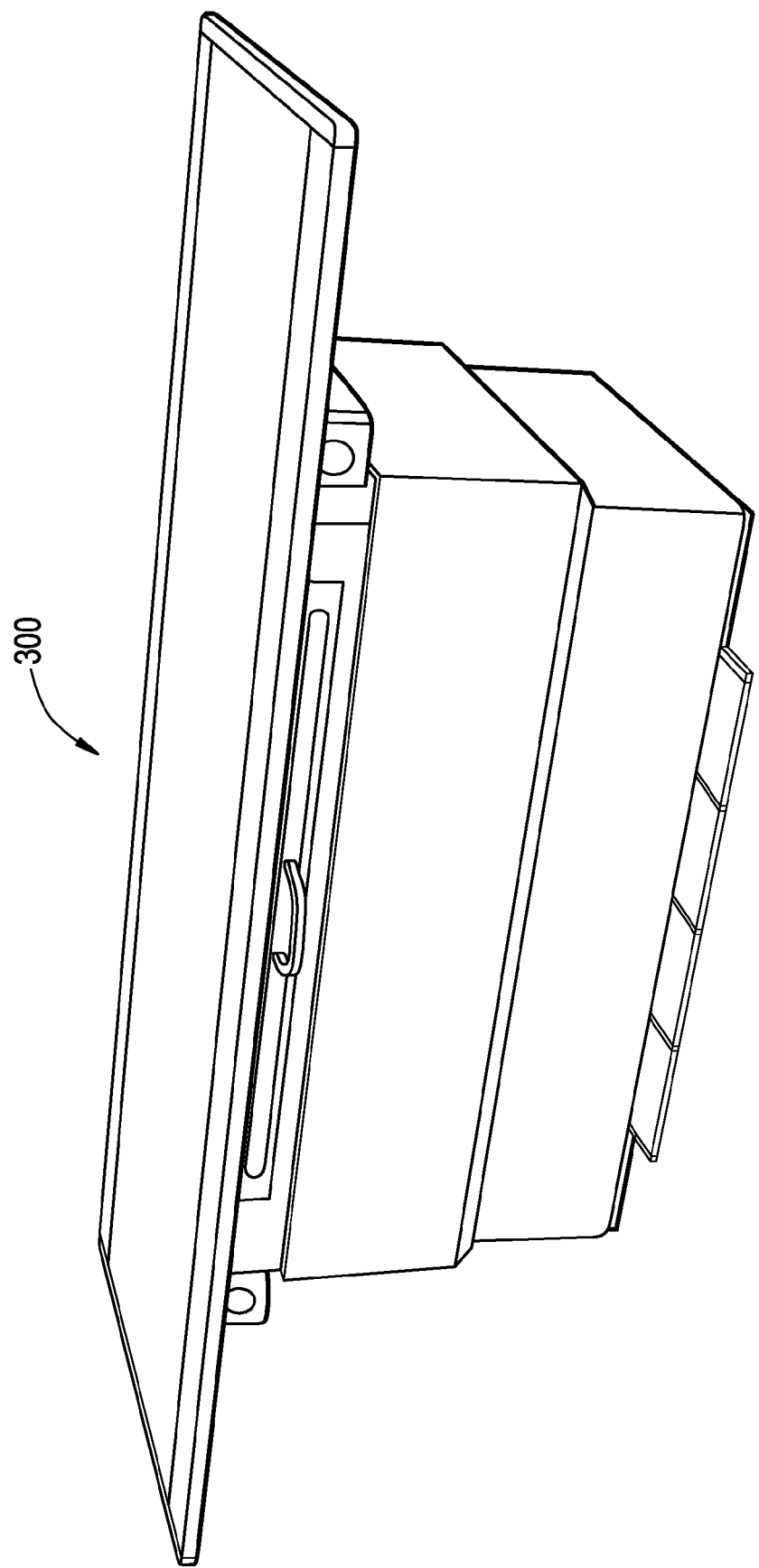
FIG. 4 is a diagram showing an example of the appearance of a radiographing table.

The radiographing table 300 has a top board 310. The radiographing table 300 is an example of the table in the present invention. The top board 310 of the radiographing table 300 is a horizontal board and is movable vertically with respect to the floor. A subject is rested on the top board 310. An X-ray receiver 340 is disposed under the top board 310. The X-ray receiver 340 is an example of the X-ray receiver in the present invention. FIG. 4 shows the appearance of an example of the radiographing table 300.

The X-ray receiver is movable horizontally. The vertical movement of the top board 310 and the horizontal movement of the second X-ray receiver 340 are each performed by utilizing power of a motor for example.

The camera 400 functions to pick up an optical image. For example, there is used a digital camera. The camera 400 is used to pick up an optical image of the subject before the radiographing.

The operator console 500 controls the X-ray irradiating unit 100, X-ray receiving unit 200 and radiographing table 300. As to the X-ray irradiating unit 100, the operator console 500 performs auto-positioning of the X-ray irradiator 120 and controls the intensity of X-ray, as well as irradiation time and irradiation timing. As to auto-positioning of the X-ray irradiator 120, a description will be given again later.

As to the X-ray receiving unit 200, the operator console 500 performs auto-positioning of the first X-ray receiver 240. As to the radiographing table 300, the operator console 500 not only controls raising and lowering of the top board 310 but also performs auto-positioning of the second X-ray receiver 340. Auto-positioning of the first X-ray receiver 240 is performed when radiographing the subject with use of the first X-ray receiver 240, while auto-positioning of the second X-ray receiver 340 is performed when radiographing the subject with use of the second X-ray receiver 340. As to auto-positioning of the first X-ray receiver 240 and that of the second X-ray receiver 340, a description will be given again later.

A signal detected by the first X-ray receiver 240 is inputted to the operator console 500. In accordance with the input signal from the first X-ray receiver 240 the operator console 500 re-construct a radioscopic image of the subject and displays it on a display 510. The X-ray receivers 240 and 340 may be formed of a photosensitive material sensitive to X-ray. In this case, the radioscopic image rendered visible by a developing process.

An optical image picked up by the camera 400 is inputted to the operator console 500. The operator console 500 analyses the optical image and specifies physical characteristics of the subject. The specified physical characteristics are, for example, stature, body thickness, style and skin condition. The operator console 500 utilizes there physical characteristics in the auto-positioning of the X-ray irradiator 120 and X-ray receivers 240 and 340.

Figure 5:
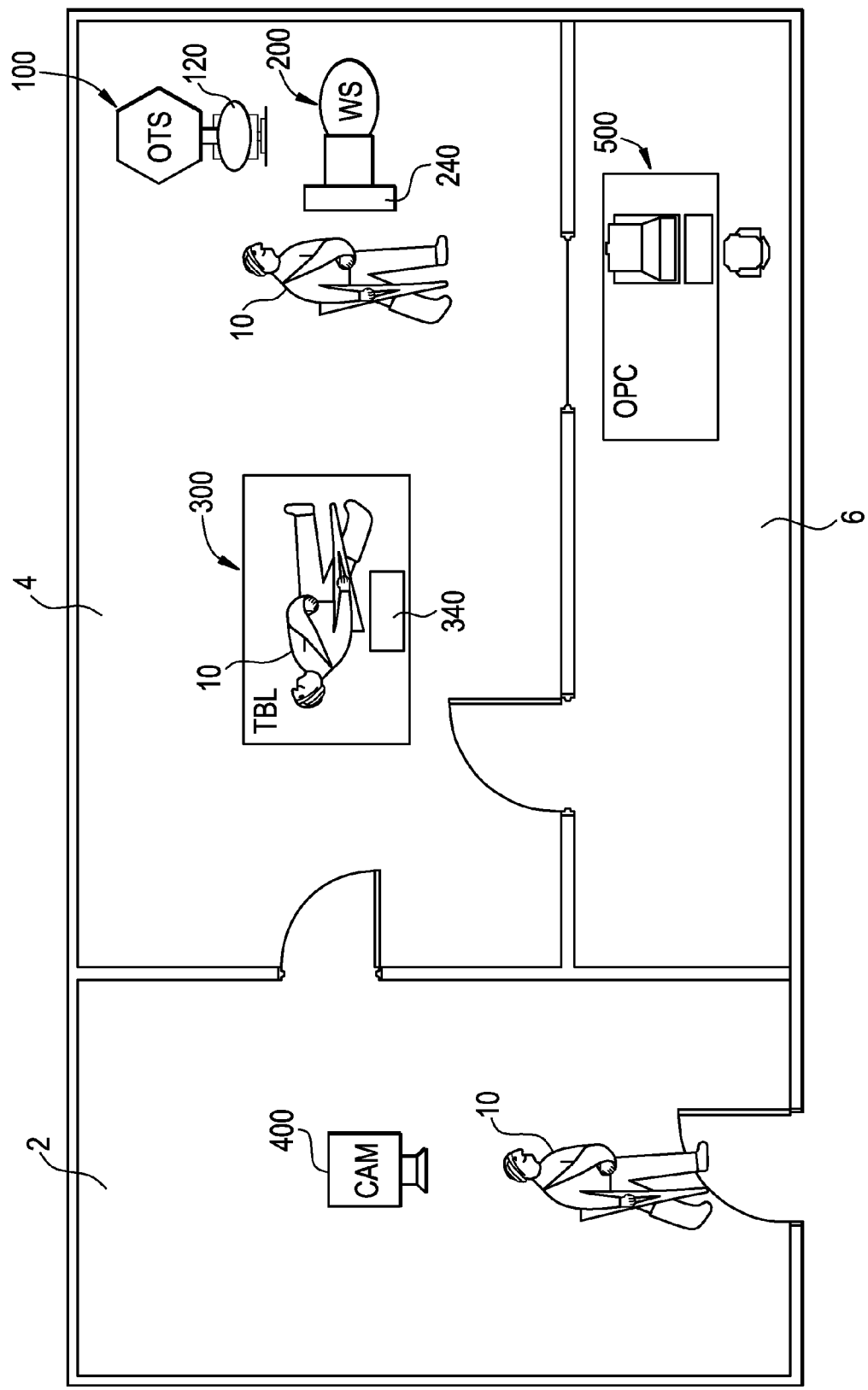
FIG. 5 is a diagram showing the plan of a radiographing chamber and a layout example of various components in the chamber.

FIG. 5 shows the plan of a radiographing chamber and a layout example of various components. As shown in FIG. 5, the radiographing chamber has a preparation compartment 2, a shielded compartment 4 and an operation compartment 6. These compartments have respective doors for entrance and exit among them. The shielded compartment 4 is shielded with lead plates or the like to prevent leakage of X-ray to the exterior. The shielded compartment 4 is provided with a window so that the interior thereof can be observed from the operation compartment 6 side. This window also possesses X-ray shieldability.

The camera 400 is installed in the preparation compartment 2. The X-ray irradiating unit 100, X-ray receiving unit 200 and radiographing table 300 are installed in the shielded compartment 4. In the operation compartment 6, the operator console 500 is installed by the window of the shielded compartment 4.

A subject 10 first enters the preparation compartment 2, in which an optical image thereof is picked up. Thereafter, the subject enters the shielded compartment 6. In the shielded compartment 6, the subject either stands up before the X-ray receiving unit 200 or lies down on the radiographing table 300.

Figure 6:
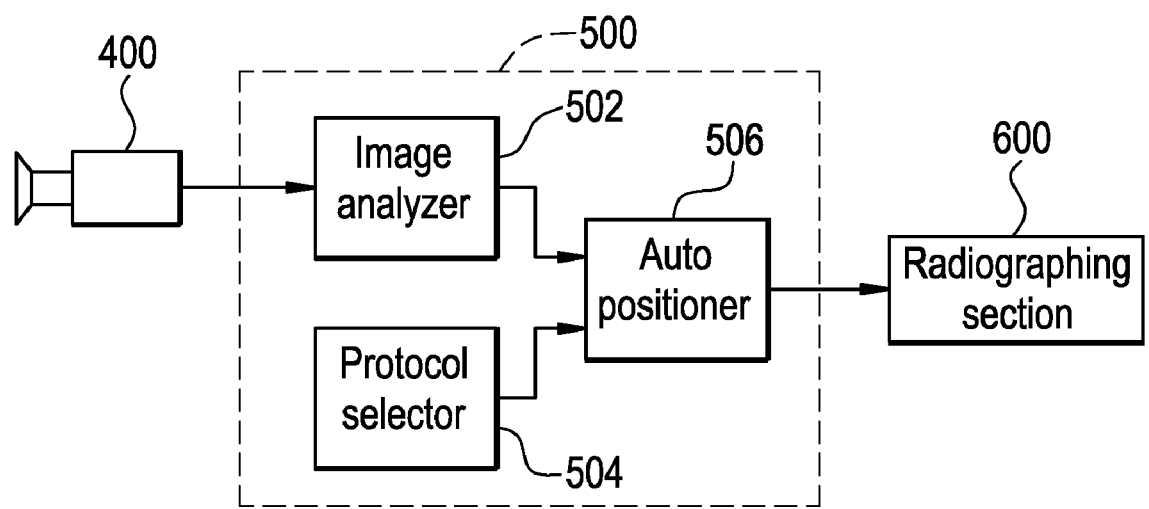
FIG. 6 is a block diagram from the standpoint of auto-positioning of the X-ray imaging system as an example of the best mode for carrying out the present invention.

FIG. 6 is a block diagram of this system as seen from the standpoint of auto positioning. The operator console 500 has an image analyzer 502, a protocol selector 504 and an auto-positioner 506.

An optical image picked up by the camera is inputted to the image analyzer 502. The image analyzer 502 analyzes the optical image and specifies physical characteristics of the subject. The specifying of physical characteristics is performed using, for example, an expert system. The specified physical characteristics are inputted to the auto-positioner 506. The image analyzer 502 is an example of the specifying device in the present invention.

In accordance with operation performed by an operator the protocol selector 504 selects, for example, head, breast, abdomen, or extremities. Information indicative of the selected portion to be radiographed is inputted to the auto-positioner 506.

The auto-positioner 506 outputs a signal based on the physical characteristics of the subject and the information on the portion to be radiographed to effect auto-positioning of a radiographing section 600. The auto-positioner 506 is an example of the positioning device in the present invention. The radiographing section 600 is made up of the X-ray irradiating unit 100, X-ray receiving unit 200 and radiographing table 300.

FIG. 7 is a flow chart showing operations of this system. As shown in FIG. 7, an optical image pick-up operation is performed in step 71. This is done using the camera 400. In this way there is obtained an optical image of the subject 10.

In step 72 there is performed specifying of physical properties. This is done by analyzing the optical image of the subject 10 in the image analyzer 502. In this way there are specified, for example, stature, body thickness, style and skin condition.

In step 73 there is performed protocol selection. This is done by the protocol selector 504 on the basis of operation performed by the operator. In this way there is selected, for example, head, breast, abdomen, or extremities, as the portion to be radiographed.

In step 74 there is performed auto-positioning. This is done by the auto-positioner 506. In order that the to-be-radiographed portion designated by the protocol selection can be radiographed, the auto-positioner 506 not only adjusts the position and angle of the X-ray irradiator 120 in conformity with the stature, body thickness, style, etc. of the subject 10 but also adjusts the position of the first X-ray receiver 240 or 340 in conformity with the position and angle of the X-ray irradiator 120. As to the first X-ray receiver 240, the direction of its light receiving surface is also adjusted.

Thus, positioning of the X-ray irradiator 120, X-ray receiver 240 and X-ray receiver 340 is performed automatically in accordance with physical characteristics of the subject 10 and the portion to be radiographed of the subject. Therefore, the system can thoroughly cope with various subjects different in stature, body thickness, style, etc.

In step 75 there is performed radiographing. The radiographing is performed under control by the operator console 500. The operator console 500 performs radiographing while matching radiographing conditions such as tube voltage, tube current, irradiation time and irradiation timing to the purpose of radiographing. The physical characteristics specified in step 72, e.g., body thickness, can be utilized for setting the radiographing conditions.

The age inputted at the time of patient registration may be utilized for setting the radiographing conditions. The age can also be utilized for determining a bone density from X-ray transmittance. There may be adopted a method wherein the state of respiration is monitored using a sensor attached to a patient and X-ray is radiated in conformity with a gentle respiration period. Further, the state of skin obtained by image analysis may be utilized in for example estimating the condition of a disease.

The invention claimed is:

1. An X-ray imaging system comprising:
    a radiographing device comprising an X-ray irradiator and an X-ray receiver positioned opposite said X-ray irradiator across an imaging space, said radiographing device configured to radiograph a subject positioned between said X-ray irradiator and said X-ray receiver;
    an optical radiographing device configured to detect an optical image of the subject;
    a specifying device configured to analyze the optical image and to specify physical characteristics of the subject; and
    a positioning device configured to position said X-ray irradiator and said X-ray receiver based on the specified physical characteristics and a portion of the subject to be radiographed.

2. An X-ray imaging system according to claim 1, wherein said radiographing device further comprises:
    a first support device configured to movably support said X-ray irradiator in two horizontal directions orthogonal to each other and in a vertical direction and to rotatably support said X-ray irradiator about two axes orthogonal to each other; and
    a second support device configured to support said X-ray receiver such that said X-ray receiver is vertically movable to facilitate changing a direction of a light receiving surface of said X-ray receiver.

3. An X-ray imaging system according to claim 2, wherein said first support device comprises an overhead tube suspension.

4. An X-ray imaging system according to claim 2, wherein said second support device comprises a wall stand.

5. An X-ray imaging system according to claim 1, wherein said radiographing device further comprises:
    a first support device configured to movably support said X-ray irradiator in two horizontal directions orthogonal to each other and in a vertical direction and to rotatably support said X-ray irradiator about two axes orthogonal to each other; and
    a table configured to support a top board as a vertically movable subject carrier and to support said X-ray receiver under the top board horizontally movably.

6. An X-ray imaging system according to claim 5, wherein said first support device comprises an overhead tube suspension.

7. An X-ray imaging system according to claim 1, wherein said X-ray receiver comprises a first X-ray receiver and a second X-ray receiver, and wherein said radiographing device further comprises:
    a first support device configured to movably support said X-ray irradiator in two horizontal directions orthogonal to each other and in a vertical direction and to rotatably support said X-ray irradiator about two axes orthogonal to each other;
    a second support device configured to support said X-ray receiver such that said X-ray receiver is vertically movable to facilitate changing a direction of a light receiving surface of said X-ray receiver; and
    a table configured to support a top board as a vertically movable subject carrier and to support said second X-ray receiver under the top board horizontally movably.

8. An X-ray imaging system according to claim 7, wherein said first support device comprises an overhead tube suspension.

9. An X-ray imaging system according to claim 7, wherein said second support device comprises a wall stand.

10. An X-ray imaging method comprising:
    picking up an optical image of the subject;
    analyzing the optical image and specifying physical characteristics of the subject;
    positioning an X-ray irradiator and an X-ray receiver based on the specified physical characteristics and a portion of the subject to be radiographed;
    radiographing the subject using the positioned X-ray irradiator and X-ray receiver.

11. An X-ray imaging method according to claim 10, wherein positioning an X-ray irradiator comprises positioning the X-ray irradiator by displacement in two horizontal directions orthogonal to each other and in a vertical direction and by rotation about two axes orthogonal to each other.

12. An X-ray imaging method according to claim 11, wherein the X-ray irradiator is supported by an overhead tube suspension.

13. An X-ray imaging method according to claim 10, wherein positioning an X-ray receiver comprises positioning the X-ray receiver by displacement in a vertical direction to facilitate changing a direction of a light receiving surface of the X-ray receiver.

14. An X-ray imaging system according to claim 13, wherein the X-ray receiver is supported by a wall stand.

15. An X-ray imaging method according to claim 10, wherein the X-ray receiver is provided under a top board as a subject carrier, and wherein positioning the X-ray receiver comprises displacing the X-ray receiver horizontally under the top board.

16. An X-ray imaging method according to claim 10, wherein the X-ray receiver includes a first X-ray receiver and a second X-ray receiver, and wherein positioning the X-ray receiver comprises positioning the first X-ray receiver and the second X-ray receiver respectively.

17. An X-ray imaging method according to claim 16, wherein positioning the first X-ray receiver comprises positioning the first X-ray receiver by displacement in a vertical direction to facilitate changing a direction of a light receiving surface of the first X-ray receiver.

18. An X-ray imaging system according to claim 17, wherein the X-ray receiver is supported by a wall stand.

19. An X-ray imaging method according to claim 16, wherein the second X-ray receiver is provided under a top board as a subject carrier, and wherein positioning the second X-ray receiver comprises displacing the second X-ray receiver horizontally under the top board.

20. An X-ray imaging method according to claim 10, wherein the X-ray irradiator is supported by an overhead tube suspension.

* * * * *